(12) United States Patent
Liu et al.

(10) Patent No.: US 11,826,736 B2
(45) Date of Patent: Nov. 28, 2023

(54) CATALYTIC CARBON FIBER PREPARATION METHODS

(71) Applicant: Merichem Company, Houston, TX (US)

(72) Inventors: Zhouyang Liu, Pearland, TX (US); Nachiketa Anand, Katy, TX (US)

(73) Assignee: Merichem Company, Houston, TX (US)

( * ) Notice: Subject to any disclaimer, the term of this patent is extended or adjusted under 35 U.S.C. 154(b) by 134 days.

(21) Appl. No.: 17/536,850

(22) Filed: Nov. 29, 2021

(65) Prior Publication Data

US 2023/0166243 A1    Jun. 1, 2023

(51) Int. Cl.
| | | |
|---|---|---|
| *B01J 27/20* | (2006.01) | |
| *B01J 37/24* | (2006.01) | |
| *B01J 37/36* | (2006.01) | |
| *B01J 37/04* | (2006.01) | |
| *B01J 31/02* | (2006.01) | |
| *C12P 17/18* | (2006.01) | |
| *B01J 31/18* | (2006.01) | |

(52) U.S. Cl.
CPC ........... *B01J 27/20* (2013.01); *B01J 31/0232* (2013.01); *B01J 31/183* (2013.01); *B01J 37/04* (2013.01); *B01J 37/24* (2013.01); *B01J 37/36* (2013.01); *C12P 17/182* (2013.01); *B01J 2231/005* (2013.01); *B01J 2531/845* (2013.01)

(58) Field of Classification Search
CPC . B01J 21/18; B01J 21/185; B01J 27/20; B01J 31/0232; B01J 31/183; B01J 37/04; B01J 37/24; B01J 37/36; B01J 2231/005; B01J 2531/845; C12P 17/182

USPC .............................................. 502/7, 163, 180
See application file for complete search history.

(56) References Cited

U.S. PATENT DOCUMENTS

| | | |
|---|---|---|
| 3,977,829 A | 8/1976 | Clonts |
| 4,666,689 A | 5/1987 | Maple et al. |
| 5,866,434 A | 2/1999 | Massey |
| 5,961,819 A | 10/1999 | Lee et al. |
| 7,029,573 B2 | 4/2006 | Greaney et al. |
| 7,875,185 B2 | 1/2011 | Zhang |
| 8,454,824 B2 | 6/2013 | Zhang et al. |

(Continued)

FOREIGN PATENT DOCUMENTS

| | | |
|---|---|---|
| CN | 103572591 | 2/2014 |
| CN | 103721747 | 4/2014 |

(Continued)

OTHER PUBLICATIONS

Pradeep K. Prajapati et al., "Covalently immobilized cobalt Phthalocyanine@MWCNT PDMS hollow fiber membrane for highly selective, reversible and bio-inspired oxygen transport." Journal of Membrane Science 624, pp. 1-11. (Year: 2021).*

(Continued)

*Primary Examiner* — Patricia L. Hailey
(74) *Attorney, Agent, or Firm* — C. Tumey Law Group PLLC

(57) ABSTRACT

A method of producing a catalytic carbon fiber may include: providing a carbon fiber and an aminated macrocycle, mixing the carbon fiber and the aminated macrocycle with a solvent; and reacting the carbon fiber and the aminated macrocycle to form an amide bond between the carbon fiber and the aminated macrocycle thereby forming the catalytic carbon fiber.

22 Claims, 5 Drawing Sheets

(56) References Cited

U.S. PATENT DOCUMENTS

| | | | |
|---|---|---|---|
| 9,458,392 B2 | 10/2016 | Zhang et al. | |
| 9,815,001 B2 | 11/2017 | Massingill | |
| 11,517,889 B2 * | 12/2022 | Liu | C10G 53/14 |
| 11,524,283 B2 * | 12/2022 | Liu | B01J 37/12 |
| 2017/0369790 A1 | 12/2017 | Gomach | |

FOREIGN PATENT DOCUMENTS

| | | | | |
|---|---|---|---|---|
| CN | 103721747 | * | 6/2014 | B01J 31/22 |
| CN | 104607246 | | 5/2015 | |
| CN | 104624237 | * | 5/2015 | B01J 31/22 |
| CN | 111501329 | | 8/2020 | |
| CN | 112047326 A | * | 12/2020 | C01B 32/168 |
| JP | S61225328 | | 10/1986 | |
| JP | S646112 | | 1/1989 | |
| JP | 07324170 A | * | 12/1995 | C09B 47/0676 |
| JP | H11244365 A | * | 9/1999 | A61L 9/01 |
| WO | WO-2011137190 A1 | * | 11/2011 | B01J 31/2295 |

OTHER PUBLICATIONS

T. V. Magdesieva et al., "Electrochemical Reduction of CO2 with Transition Metal Phthalocyanine and Porphyrin Complexes Supported on Activated Carbon Fibers." Journal of The Electrochemical Society, 149 (6), pp. D89-D95. (Year: 2002).*

International Search Report and Written Opinion for Application No. PCT/US2021/064390, dated Apr. 29, 2022.

* cited by examiner

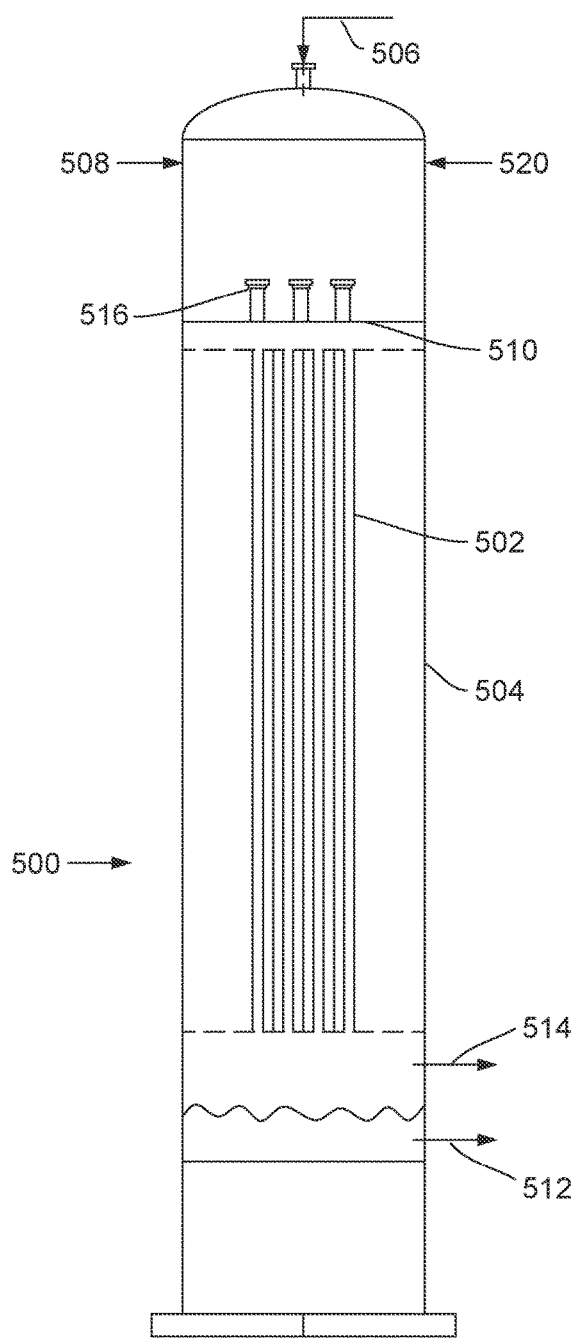
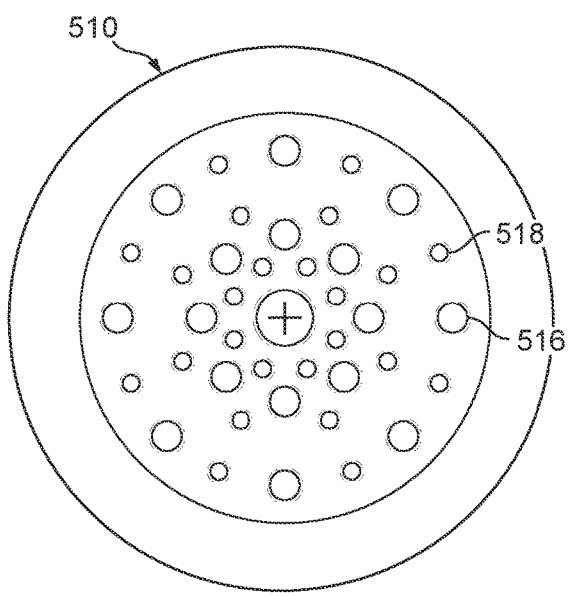
FIG. 5a
FIG. 5b

CATALYTIC CARBON FIBER PREPARATION METHODS

BACKGROUND

Chemical processes often require multiple unit operations to produce a product stream. A particular unit operation may be a liquid-liquid contacting operation whereby two liquids are brought into intimate contact to effectuate mass transfer between the liquids, a reaction between components in the liquids, or both. Another unit operation may be a gas-liquid contacting operation whereby a gas and a liquid are brought in contact to effectuate mass transfer between the liquids, a reaction between components in the liquids, or both. Liquid-liquid contacting may be beneficial in some types of chemical reactions where one reactant is miscible in a first liquid but immiscible in a second liquid. An example of such a reaction may be where a first reactant is present in a polar solvent such as water and a second reactant is present in a non-polar solvent such as a hydrocarbon and the water and hydrocarbon are immiscible. Liquid-liquid contacting may have other applications such as liquid-liquid extraction whereby a species present in a first liquid is extracted into a second liquid by mass transfer across the liquid-liquid interface. Gas-liquid contacting may be beneficial in some types of chemical reactions where a component in the gas phase is to be reacted with a component in the liquid phase of where a gaseous component is absorbed into the liquid phase.

A particular challenge of liquid-liquid contactors and gas-liquid contactors, collectively referred to as "mass transfer devices", may be ensuring adequate contact area between phases such that the mass transfer or reactions may occur in an appreciable amount and in an economically viable manner. In general, liquid-liquid contacting operations may be performed with immiscible liquids, such as, for example, an aqueous liquid and an organic liquid. Using two immiscible liquids may allow the liquids to be readily separated after the liquid-liquid contacting is completed. However, when a liquid-liquid contacting operation is performed with immiscible liquids, phase separation may occur before adequate contact between the liquids is achieved.

Several mass transfer devices and techniques have been developed to enhance the contact area between phases, including, but not limited to, fiber-bundle type contactors. A fiber-bundle type contactor may generally comprise one or more fiber bundles suspended within a shell and two or more inlets where the phases, including gas-liquid or liquid-liquid, may be introduced into the shell. The fiber bundle may promote contact between the phases by allowing a first phase to flow along individual fibers of the fiber bundles and a second phase to flow between the individual fibers thereby increasing the effective contact area between the phases. The two phases may flow from an inlet section of the shell to an outlet section of the shell while maintaining intimate contact such that a reaction, mass transfer, or both may be maintained between the two phases.

Fiber-bundle type contactors have been developed to teat mercaptan sulfur containing hydrocarbon streams. In these contactors, a liquid catalyst or solid catalyst bed may be utilized in conjunction with caustic to convert mercaptan sulfur to disulfide oil. However, there exist challenges in this process including ensuring that the extent of reaction is sufficient to such that the resultant product stream is on specification. Some methods to ensure that the extent of reaction are sufficient to produce a product stream that is on specification may be to design the mass transfer device to have longer contact time by building the mass transfer device physically larger or to design the mass transfer device with features that enhance mixing from entrance effects. While physical features of the mass transfer device may be optimized to some degree, there may be limitations to the extent to which a reaction may proceed regardless of the physical configuration of the mass transfer device because of limitations of the oxidation catalyst.

SUMMARY

In an embodiment a method of producing a catalytic carbon fiber may include: providing a carbon fiber and an aminated macrocycle, mixing the carbon fiber and the aminated macrocycle with a solvent; and reacting the carbon fiber and the aminated macrocycle to form an amide bond between the carbon fiber and the aminated macrocycle thereby forming the catalytic carbon fiber. In another embodiment, a method of producing a catalytic carbon fiber may include: providing a carbon fiber; reacting the carbon fiber with a chlorinating agent to produce a carbon fiber comprising acyl chloride; and reacting the carbon fiber comprising acyl chloride with an aminated macrocycle to form an amide bond between the carbon fiber comprising acyl chloride and the aminated macrocycle thereby forming the catalytic carbon fiber. In another embodiment, a method of producing a catalytic carbon fiber may include: providing a carbon fiber; reacting the carbon fiber with a coupling agent to produce a functionalized carbon fiber; and reacting the functionalized carbon fiber with an aminated macrocycle to form an amide bond between the carbon fiber and the aminated macrocycle thereby forming the catalytic carbon fiber. Another embodiment may include a method of producing a catalytic carbon fiber may include providing a carbon fiber; providing an enzyme capable of catalyzing an amide bond formation; and reacting the carbon fiber with an aminated macrocycle in the presence of the enzyme to form a bond between the carbon fiber and the aminated macrocycle thereby forming the catalytic carbon fiber.

BRIEF DESCRIPTION OF THE DRAWINGS

These drawings illustrate certain aspects of some of the embodiments of the present disclosure, and should not be used to limit or define the disclosure.

FIG. 5a illustrates a standalone caustic regeneration unit containing catalytic carbon fibers FIG. 5b illustrates a top view of a distributor tray.

DETAILED DESCRIPTION

Figure 1:
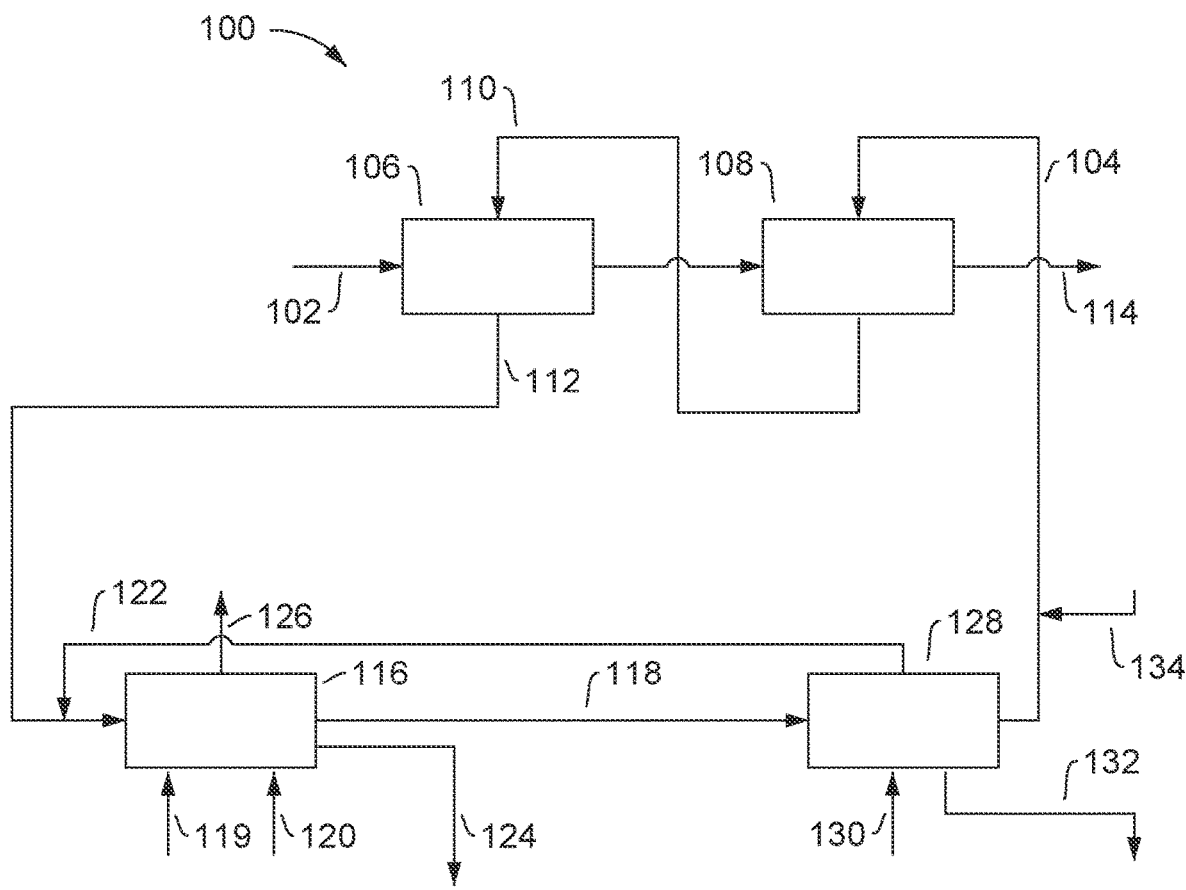
FIG. 1 is a block flow diagram of a process for producing disulfide oil from a hydrocarbon stream containing mercaptan sulfur.

The present disclosure may relate to liquid-liquid and gas-liquid mass transfer devices, and in some embodiments, to mass transfer devices comprising catalytic carbon fibers. Catalytic carbon fibers may comprise an organometallic catalyst that has been chemically grafted onto a surface of a carbon fiber. The catalytic carbon fiber may be used as a heterogeneous catalyst in the liquid-liquid and gas-liquid mass transfer devices.

The catalytic carbon fibers may be prepared by reacting an aminated macrocycle with carbon fiber in the presence of a solvent to produce the catalytic carbon fibers. Any type of carbon fiber may be utilized in the present disclosure including, but not limited to, carbon fibers prepared using polyacrylonitrile (PAN), mesophase pitch, and rayon. Suitable carbon fibers may have any structural ordering including those carbon fibers classified as turbostratic or graphitic or any structural ordering therebetween. Carbon fibers may be of any quality including from about 50% carbon by weight to about 100% carbon by weight any may have any classification such as low modulus carbon fiber having a tensile strength modulus below 240 million kPa, intermediate modulus carbon fiber having a tensile strength modulus of about 240 million kPa to 500 million kPa, or high tensile strength modulus carbon fiber having a tensile strength modulus of about 500 million-1.0 billion kPa. Carbon fibers may have any diameter including from about 5 micrometers to about 20 micrometers, or any diameters therebetween. Carob fibers may be in the form of yarns or bundles whereby several hundred to several thousand individual carbon fibers may be spun together to form the carbon fiber yarn or carbon fiber bundle.

The aminated macrocycle may comprise an organometallic macrocycle and amine group grafted to the organometallic macrocycle. The amine group may include an amino group, and imino group, or combinations thereof. The amine group allows the aminated macrocycle to react with oxygen-containing groups such as carboxylic groups on the surface of the carbon fiber to form an amide bond between the aminated macrocycle and the carbon fiber. Carbon fiber production may include surface treatment steps that leave carboxylic groups on the surface of the carbon fiber. The concentration of carboxylic groups may determine the amount of aminated macrocycle that may be reacted with the carbon fiber. Further oxidative surface treatments may be utilized to increase the concentration of reactive groups, including carboxylic groups, such that the carbon fiber may react with greater amounts of aminated macrocycle.

Carbon fiber oxidation may be carried out in a liquid or gas environment to form oxygen-containing functional groups on the surface of the carbon fiber. Oxygen-containing functional groups may include carboxyl, carbonyl, lactone, and hydroxyl which are covalently bonded to at least a portion of the carbon atoms making up the carbon fiber. The step of oxidizing may oxidize the carbon fiber to any suitable extent. Without limitation, the carbon fiber may be oxidized to include about 0.1 wt. % to about 25 wt. % oxygen-containing functional groups. Alternatively, the carbon fiber may be oxidized to include about 0.1 wt. % to about 1 wt. % oxygen-containing functional groups, about 1 wt. % to about 5 wt. % oxygen-containing functional groups, about 5 wt. % to about 10 wt. % oxygen-containing functional groups, about 10 wt. % to about 15 wt. % oxygen-containing functional groups, about 15 wt. % to about 20 wt. % oxygen-containing functional groups, about 20 wt. % to about 25 wt. % oxygen-containing functional groups, or any ranges therebetween. The degree of oxidation may be utilized to control the final concentration organometallic macrocycle dispersed on the catalytic carbon fiber which may in turn directly affect the overall catalytic activity of the catalytic carbon fiber.

Oxidation of the carbon fiber may be achieved by submersing the virgin carbon fiber in an acid and allowing the acid to react with the virgin carbon fiber. Suitable acids may include mineral acids such as hydrochloric acid, nitric acid, phosphoric acid, sulfuric acid, boric acid, hydrofluoric acid, hydrobromic acid, perchloric acid, hydroiodic acid, fluoroantimonic acid, carborane acids, fluoroboric acid, fluorosulfuric acid, hydrogen fluoride, triflic acid, and perchloric acid for example organic acids such as acetic acid, formic acid, citric acid, oxalic acid, and tartaric acid, for example. In addition to, or alternatively to oxidation using acids, the oxidation step may also be performed using plasma treatment in oxygen atmosphere, gamma radiation treatment, electrochemical oxidation using an oxidant such as sodium hydroxide, ammonium hydrogen carbonate, ammonium carbonate, sulfuric acid, or nitric acid, or oxidation by potassium persulfate with sodium hydroxide or silver nitrate. The acidic oxidation may be performed at any temperature in the range of about 0° C. to 150° C. Alternatively, the oxidation may be performed in a range of 0° C. to about 25° C., about 25° C. to about 50° C., about 50° C. to about 75° C., about 75° C. to about 100° C., about 100° C. to about 125° C., about 125° C. to about 150° C. or any temperature ranges therebetween. Oxidation may be performed for any period of time suitable for achieving a desired concentration of oxygen-containing functional groups on the carbon fibers. The time required to achieve a specified concentration of oxygen-containing functional groups may be dependent upon many factors including identity and concentration of the acid and temperature conditions selected. In general, the oxidation may be carried out for a period of time ranging from about 1 hour to about 24 hours. Alternatively, the oxidation may be carried out in a time ranging from about 1 hour to about 3 hours, about 3 hours to about 6 hours, about 6 hours to about 9 hours, about 9 hours to about 12 hour, about 12 hours to about 15 hours, about 15 hours to about 18 hours, about 18 hours to about 21 hours, about 21 hours to about 24 hours, or any ranges therebetween. After oxidation by acid treatment, the oxidized carbon fibers may optionally be washed using water or other solvent to remove excess acid. The oxidized carbon fibers may be dried at elevated temperature after washing to remove water or solvent used in the washing step.

The aminated macrocycle may include any suitable organometallic macrocycle, including, but not limited to, unsubstituted metal phthalocyanines, substituted metal phthalocyanines, and combinations thereof. Substituted metal phthalocyanine may include substitutions of halogens, hydroxyl, alkyl, aryl, thiol, alkoxy, nitrosyl groups, or combinations thereof, at one or more peripheral hydrogen atoms on the metal phthalocyanine. Metal phthalocyanines may include any suitable metal including, without limitation, vanadium (V), manganese (Mn), iron (Fe), cobalt (Co), nickel (Ni), copper (Cu), zinc (Zn), ruthenium (Ru), rhodium (Rh), palladium (Pd), silver (Ag), and combinations thereof. The aminated macrocycle may include one or more amine groups (—$NH_2$ or —NH) grafted to the organometallic macrocycle. The aminated macrocycle may include an amine containing compound grafted to the organic macrocycle. The amine containing compounds may include C2-C20, monoamines, diamines, triamines, and higher order amines. The amine containing compound may include linear, branched, or cyclic amines. Some specific amine containing compounds may include, without limitation, ethylenediamine, propane-1,3-diamine, butane-1,4-diamine, pentane-1,5-diamine, hexamethylenediamine, diethylenetriamine, benzene-1,3,5-triamine, and combinations thereof. Some suitable aminated macrocycles may include amino cobalt phthalocyanines such as mono amino cobalt phthalocyanines and poly amino cobalt phthalocyanines. Poly amino cobalt phthalocyanines may include di-amino cobalt phthalocyanine, tri-amino cobalt phthalocyanines, tetra-amino cobalt phthalocyanines, and higher order poly amino cobalt phthalocyanines. Other specific suitable aminated macrocycles may include porphyrins, hemes, polyaza compounds, and crown ethers.

Catalytic carbon fibers may be prepared by reacting an aminated macrocycle with carbon fiber to form an amide bond between the aminated macrocycle. There are several synthesis methods for formation of an amide bond between the carbon fiber and the aminated macrocycle, only some of which may be disclosed herein. One synthesis method may include direct formation of the amide bond by reacting the carbon fiber and aminated macrocycle at elevated temperature in a suitable solvent. Another synthesis method may include amide formation via the generation of acyl chlorides from carboxylic acids with chlorinating agents such as thionyl chloride. Another synthesis method may include amide formation using a coupling agent such as carbodiimide or benzotriazole. Another synthesis method may include enzyme catalyzed amide formation.

In the direct amide bond synthesis, carbon fiber and aminated macrocycle may be combined in a solvent and heated thereby forming an amide bond between the carbon fiber and aminated macrocycle to produce the catalytic carbon fiber. Some suitable solvents may include, but are not limited to pyridine, DMSO, DMF, THF, ethanol, acetonitrile, chloroform, ethylene glycol, methanol, benzene, and combinations thereof. The carbon fibers may be reacted with the aminated macrocycle at any suitable conditions, including at a temperature in the range of about 100° C. to 200° C. Alternatively, the reaction may be performed in a range of 100° C. to about 125° C., about 125° C. to about 150° C., about 150° C. to about 175° C., about 175° C. to about 200° C., or any temperature ranges therebetween. The time required for reacting the carbon fibers and aminated macrocycle may be dependent upon many factors including identity of the aminated macrocycle and temperature conditions selected. In general, the carbon fibers may be reacted with the aminated macrocycle for a period of time ranging from about 1 hour to about 24 hours or longer. Alternatively, the reaction may be carried out in a time ranging from about 1 hour to about 3 hours, about 3 hours to about 6 hours, about 6 hours to about 9 hours, about 9 hours to about 12 hour, about 12 hours to about 15 hours, about 15 hours to about 18 hours, about 18 hours to about 21 hours, about 21 hours to about 24 hours, or any ranges therebetween. After the aminated macrocycle reaction, the catalytic carbon fiber may optionally be washed using water or other solvent to remove excess aminated macrocycle. The catalytic carbon fiber may be dried at elevated temperature after washing to remove water or solvent used in the washing step.

In the acyl chloride synthesis, carbon fiber may be combined with a chlorinating agent such as thionyl chloride, phosphorous trichloride, or terephthaloyl chloride, and heated. The chlorinating agent may react with oxygen containing groups, such as carboxylic groups, on the carbon fiber to produce acyl chloride on the carbon fiber. The carbon fibers may be reacted with the chlorinating agent at any suitable conditions below the boiling point of the chlorinating agent, including at a temperature in the range of about 0° C. to 150° C. Alternatively, the reaction may be performed in a range of 0° C. to about 25° C., about 25° C. to about 50° C., about 50° C. to about 75° C., about 75° C. to about 100° C., about 100° C. to about 125° C., about 125° C. to about 150° C. or any temperature ranges therebetween.

In general, the carbon fibers may be reacted with the chlorinating agent for a period of time ranging from about 1 hour to about 24 hours or longer. The chlorinating agent modified carbon fibers may be reacted with an aminated macrocycle to produce a catalytic carbon fiber. For example, the chlorinating agent modified carbon fibers and aminated macrocycle may be combined in a solvent and heated thereby forming an amine bond between the carbon fiber and aminated macrocycle to produce the catalytic carbon fiber. Some suitable solvents may include, but are not limited to water, pyridine, DMSO, DMF, THF, ethanol, acetonitrile, chloroform, ethylene glycol, methanol, benzene, and combinations thereof. The chlorinating agent modified carbon fibers may be reacted with the aminated macrocycle at any suitable conditions, including at a temperature in the range of about 0° C. to 150° C. Alternatively, the reaction may be performed in a range of 0° C. to about 25° C., about 25° C. to about 50° C., about 50° C. to about 75° C., about 75° C. to about 100° C., about 100° C. to about 125° C., about 125° C. to about 150° C. or any temperature ranges therebetween. The time required for reacting the chlorinating agent modified carbon fibers and aminated macrocycle may be dependent upon many factors including identity of the aminated macrocycle and temperature conditions selected. In general, the chlorinating agent modified carbon fibers may be reacted with the aminated macrocycle for a period of time ranging from about 1 hour to about 24 hours or longer. Alternatively, the reaction may be carried out in a time ranging from about 1 hour to about 3 hours, about 3 hours to about 6 hours, about 6 hours to about 9 hours, about 9 hours to about 12 hour, about 12 hours to about 15 hours, about 15 hours to about 18 hours, about 18 hours to about 21 hours, about 21 hours to about 24 hours, or any ranges therebetween. After the aminated macrocycle reaction, the catalytic carbon fiber may optionally be washed using water or other solvent to remove excess aminated macrocycle. The catalytic carbon fiber may be dried at elevated temperature after washing to remove water or solvent used in the washing step.

Another synthesis method may include amide formation using a coupling agent. In this method, carbon fiber and a coupling agent may be combined in a suitable solvent and heated. The coupling agent may react with oxygen-containing functional groups on the carbon fiber or with the carbon fiber to form a functionalized carbon fiber. Some suitable coupling agents may include, but are not limited to carbodiimide, benzotriazole, and combinations thereof. The functionalized carbon fiber may be combined with an aminated macrocycle and solvent which may react to form the catalytic carbon fiber. Some suitable solvents may include, but are not limited to water, pyridine, DMSO, DMF, THF, ethanol, acetonitrile, chloroform, ethylene glycol, methanol, benzene, and combinations thereof. The functionalized carbon fiber may be reacted with the aminated macrocycle at any suitable conditions, including at a temperature in the range of about 0° C. to 150° C. Alternatively, the reaction may be performed in a range of 0° C. to about 25° C., about 25° C. to about 50° C., about 50° C. to about 75° C., about 75° C. to about 100° C., about 100° C. to about 125° C., about 125° C. to about 150° C. or any temperature ranges therebetween. The time required for reacting the functionalized carbon fiber and aminated macrocycle may be dependent upon many factors including identity of the aminated macrocycle and temperature conditions selected. In general, the functionalized carbon fiber may be reacted with the aminated macrocycle for a period of time ranging from about 1 hour to about 24 hours or longer. Alternatively, the reaction may be carried out in a time ranging from about 1 hour to about 3 hours, about 3 hours to about 6 hours, about 6 hours to about 9 hours, about 9 hours to about 12 hour, about 12 hours to about 15 hours, about 15 hours to about 18 hours, about 18 hours to about 21 hours, about 21 hours to about 24 hours, or any ranges therebetween. After the aminated macrocycle reaction, the catalytic carbon fiber may optionally be washed using water or other solvent to remove excess aminated macrocycle. The catalytic carbon fiber may be dried at elevated temperature after washing to remove water or solvent used in the washing step.

Another synthesis method may include amide formation using an enzyme. Enzymatic catalysis may allow for the amination reaction to occur at relatively lower temperatures which may allow for a broader solvent compatibility. In this method, carbon fiber and aminated macrocycle may be combined in a in a suitable solvent with an enzyme. The enzyme may include any enzyme capable of catalyzing the formation of an amide bond between the carbon fiber and the animated macrocycle. Some examples of suitable enzymes may include, but are not limited to, proteases, subtilisin, acylases, amidases lipases, and combinations thereof. Some suitable solvents may include, but are not limited to water, pyridine, DMSO, DMF, THF, ethanol, acetonitrile, chloroform, ethylene glycol, methanol, benzene, and combinations thereof. The carbon fiber may be reacted with the aminated macrocycle at any suitable conditions, including at a temperature in the range of about 0° C. to 100° C. Alternatively, the reaction may be performed in a range of 0° C. to about 25° C., about 25° C. to about 50° C., about 50° C. to about 75° C., about 75° C. to about 100° C., or any temperature ranges therebetween. The time required for reacting the carbon fiber and aminated macrocycle may be dependent upon many factors including identity of the aminated macrocycle and temperature conditions selected. In general, the carbon fiber may be reacted with the aminated macrocycle for a period of time ranging from about 1 hour to about 24 hours or longer. Alternatively, the reaction may be carried out in a time ranging from about 1 hour to about 3 hours, about 3 hours to about 6 hours, about 6 hours to about 9 hours, about 9 hours to about 12 hour, about 12 hours to about 15 hours, about 15 hours to about 18 hours, about 18 hours to about 21 hours, about 21 hours to about 24 hours, or any ranges therebetween. After the aminated macrocycle reaction, the catalytic carbon fiber may optionally be washed using water or other solvent to remove excess aminated macrocycle. The catalytic carbon fiber may be dried at elevated temperature after washing to remove water or solvent used in the washing step.

Once the catalytic carbon fibers have been synthesized as described above, the catalytic carbon fibers may be further processed by shaping the catalytic carbon fibers. For example, individual strands of the catalytic carbon fibers may be drawn together and secured to form a catalytic carbon fiber bundle. The catalytic carbon fiber bundle may be utilized in a reactor to form a reaction zone within the reactor. Additional processing of the carbon fibers may include reducing the size of the carbon fibers to produce a catalytic carbon fiber suitable for fluidization, for example within a fluidized bed reactor, or may be pelletized or otherwise made suitable for use in a packed bed reactor.

Hydrocarbon streams in refineries and chemical plants often contain unwanted contaminants such as organically bound sulfur compounds, carboxylic acids, and hydrogen sulfide. Product specifications may call for the reduction and/or removal of these contaminants during the refining process. Organically bound sulfur, such as mercaptan sulfur, may be present in some hydrocarbon streams within a refinery or chemical plant. It may be desirable to reduce the mercaptan sulfur content of a hydrocarbon stream to produce a product stream with reduced mercaptan sulfur content. There are generally two options for treating mercaptan sulfur containing streams. Mercaptan extraction may be utilized whereby the mercaptan sulfur is reacted with a caustic stream to produce an organo-sulfur compound such as a mercaptide. A portion of the mercaptide may dissolve in the aqueous portion of the caustic stream thereby removing the mercaptan sulfur from the hydrocarbon stream. In general, the solubility of the organo-sulfur compound is a function of the hydrocarbon chain length whereby relatively lower molecular weight mercaptans may produce a more soluble product when reacted with the caustic stream and relatively higher molecular weight mercaptans may produce a relatively less soluble product when reacted with the caustic stream. The organo-sulfur compound may be further oxidized to disulfide oil by reacting the organo-sulfur compound with oxygen in the presence of a catalyst. For some hydrocarbon streams containing heavier mercaptan sulfur containing compounds, mercaptan sweetening may be utilized to directly convert the mercaptan sulfur to the disulfide oil by reacting the mercaptan sulfur with oxygen in the presence of a catalyst. Sweetening directly to disulfide oil may be preferable in some hydrocarbon streams where the organo-sulfur compounds produced would be relatively insoluble in the aqueous portion of the caustic stream. Some operations may involve extraction and sweetening in series whereby a mixed hydrocarbon stream containing a portion of relatively lower molecular weight mercaptan sulfur and a relatively higher molecular weight mercaptan sulfur are contacted with a caustic stream followed by oxidation to produce disulfide oil. Such operations may occur in separate units or as an integrated process within a single vessel. An example of single vessel extraction/oxidation us the Mericat™ II process available from Merichem Company.

There may be a wide variety of hydrocarbon streams which contain contaminants that may be removed. While the present application may only disclose embodiments with regards to some specific hydrocarbon streams, the disclosure herein may be readily applied to other hydrocarbon streams not specifically enumerated herein. The caustic treatment process may be appropriate for treatment of any hydrocarbon feed including, but not limited to, hydrocarbons such as alkanes, alkenes, alkynes, and aromatics, for example. The hydrocarbons may comprise hydrocarbons of any chain length, for example, from about $C_3$ to about $C_{30}$, or greater, and may comprise any amount of branching. Some exemplary hydrocarbon feeds may include, but are not limited to, crude oil, propane, LPG, butane, light naphtha, isomerate, heavy naphtha, reformate, jet fuel, kerosene, diesel oil, hydro treated distillate, heavy vacuum gas oil, light vacuum gas oil, gas oil, coker gas oil, alkylates, fuel oils, light cycle oils, and combinations thereof. Some non-limiting examples of hydrocarbon streams may include crude oil distillation unit streams such as light naphtha, heavy naphtha, jet fuel, and kerosene, fluidized catalytic cracker or resid catalytic cracker gasoline, or RCC, natural gasoline from NGL fractionation, and gas condensates.

Methods of extracting mercaptan sulfur may include contacting the hydrocarbon stream with a caustic stream containing hydroxide and reacting at least a portion of the mercaptan sulfur content of the hydrocarbon stream with the hydroxide in the caustic stream. The hydroxide may be any hydroxide capable of reacting with mercaptan sulfur. Some exemplary hydroxides may include Group I and Group II hydroxides such as NaOH, KOH, RbOH, CsOH, $Ca(OH)_2$, and Mg(OH)$_2$, for example. The hydroxide may be present in an aqueous solution in a concentration suitable for a particular application, generally from about 5 wt. % up to and including saturation.

The generalized reaction of hydroxide and mercaptan sulfur is shown in Reaction 1 where the mercaptan sulfur (RSH) reacts with hydroxide (XOH), where X is a Group I or Group II cation, to form the corresponding mercaptide (RSX) and water.

RSH+XOH→RSX+H$_2$O  Reaction 1

As discussed above, depending on the molecular weight of the mercaptan sulfur being reacted with the hydroxide, a portion of the mercaptide produced may dissolve in the aqueous portion of the caustic stream. Once the mercaptan sulfur is reacted with the caustic stream, a "spent caustic" or "rich caustic" solution containing the water, residual hydroxide, and soluble components may be generated. The spent caustic may be regenerated to form lean caustic with reduced mercaptide content for recycling back to Reaction 1. One process of regeneration may include mixing oxygen or air with the spent caustic and contacting the resultant mixture with a catalyst to regenerate the caustic stream. The generalized process of regeneration is shown in Reaction 2 where the mercaptide (RSX) reacts with water and oxygen in the presence of a catalyst produce disulfide (RSSR), also referred to as disulfide oil (DSO), caustic, and water.

$$2RSX+2H_2O+\tfrac{1}{2}O_2 \xrightarrow{Catalyst} RSSR+2XOH+H_2O$$  Reaction 2

As discussed above, one of the challenges with treatment of mercaptan sulfur is that there may be issues with extent of reaction whereby the mercaptan sulfur concentration is not reduced to the level required for the resultant product stream to be on spec. In units which utilize an extractor section and an oxidation section, such as UOP Merox™, the catalyst may be dispersed in the caustic stream which circulates through the extraction and oxidation sections of the unit. In sweetening units, the catalyst may be contained in a fixed bed within a reactor. The catalyst may be impregnated in charcoal or activated carbon where the catalyst bed may be wetted with caustic solution. In either case, the catalyst may not have enough catalytic activity and/or residence time within the reactor may be too short to effectively oxide the mercaptides. One of the exemplary uses of the catalytic carbon fibers disclosed herein is in replacing the conventional oxygenation catalysts presently utilized in the oxidation of mercaptides to produce disulfide oil. As will be discussed in detail below, catalytic carbon fibers exhibit high reactivity to oxidation of mercaptides and have desirable physical properties which are well suited for use in mercaptide oxidation reactors.

There may be a wide variety of process conditions suitable for oxidation of the mercaptides, the exact conditions of which may vary depending on the hydrocarbon feed. For lighter hydrocarbons, operating pressure may be controlled to be slightly above the bubble point to ensure liquid-phase operation. For relatively heavier hydrocarbons, pressure may be set to keep air dissolved in the oxidation section. Operating temperature may also be selected based on the hydrocarbon feed with general conditions of temperature ranging from about 20° C. to about 100° C.

FIG. 1 illustrates one embodiment of a hydrocarbon desulfurization process 100 which may utilize catalytic carbon fibers in mercaptide oxidation. In FIG. 1, hydrocarbon feed 102 containing mercaptan sulfur compounds may be treated in a counter current multiple stage caustic treatment section. Lean caustic 104 may be fed to a last stage 108 where the lean caustic extracts the mercaptans from the hydrocarbons entering last stage 108 after first being treated in first stage 106. The caustic may be removed from last stage 108 as stream 110 and may be fed to first stage 106 and be contacted with hydrocarbon feed 102. Spent caustic stream 112 may be withdrawn from first stage 106 and the treated hydrocarbon 114 may be withdrawn from last stage 108. The specific design of the caustic treatment section is not critical the functionality of the catalytic carbon fibers of the present disclosure, however, one design may include staged contactors operating in a counter-current configuration as schematically illustrated in FIG. 1, and another design may be using fiber film liquid-liquid contactor to assist in the mass transfer of the mercaptans from the hydrocarbon feed 102 into the caustic treatment solution.

Spent caustic 112 withdrawn from first stage 106 and oxidizer 118 may be fed to oxidation section 116. Oxidizer 118 may include any suitable oxidizer, including air, oxygen, hydrogen peroxide, or any other oxygen containing gas or compound which releases oxygen. Oxidation section 116 may include catalytic carbon fibers disclosed herein capable of oxidizing mercaptides present in spent caustic 112 to form disulfide oil. The mercaptides, water, and oxygen in spent caustic 112 may react according to Reaction 2 in the presence of the catalytic carbon fibers to produce disulfide oil, regenerated caustic, and water. The regenerated caustic may be drawn off as regenerated caustic stream 118 and the disulfide oil may be drawn off as disulfide stream 124. Off-gas steam 126 containing residual gaseous hydrocarbons, air, oxygen, or other gasses may be withdrawn from oxidation section 116 and sent to a downstream unit for further processing or to flare as needed.

As the conditions within oxidation section 116 may be conducive to forming an explosive mixture with combinations of hydrocarbon and oxidizer, it may be desired to operate the oxidation section 116 such that the gasses present in oxidation section 116 are below the lower explosive limit (LEL) or above the upper explosive limit (UEL). A gas stream 120 may optionally be introduced into oxidation section 116 such that the LEL/UEL conditions are maintained. Gas stream 120 may include fuel gas, inert gas, or any other suitable gas to control LEL/UEL. Another alternative may be the inclusion of solvent stream 122 into oxidation section 116. Solvent stream 122 may be from any source but should preferably contain little to no disulfide oil. Solvent stream 122 may be mixed with spent caustic stream 112 prior to entering the oxidation section 116 or it may be injected as a separate stream into the bottom of oxidation section 116. The solvent may be any light hydrocarbon or mixture of light hydrocarbons such as naphtha and kerosene that will assist in the separation of the disulfide oil from the caustic solution after oxidation of the mercaptans. The disulfide oil may have a higher solubility in the DSO as compared to the aqueous portion of spent caustic 112, with their differential of solubility providing an extractive driving force for the DSO. In examples where a solvent is utilized, the solvent may be drawn off with the disulfide oil in disulfide stream 124.

In some examples, regenerated caustic stream 118 may be further purified in solvent wash section 128 whereby a solvent stream 130 may contact regenerated caustic stream 118 to further remove DSO from the regenerated caustic stream 118. A Spent caustic stream 132 may be withdrawn from solvent wash section 128 and additional fresh caustic from fresh caustic stream 134 may be added to form lean caustic 104.

Figure 2:
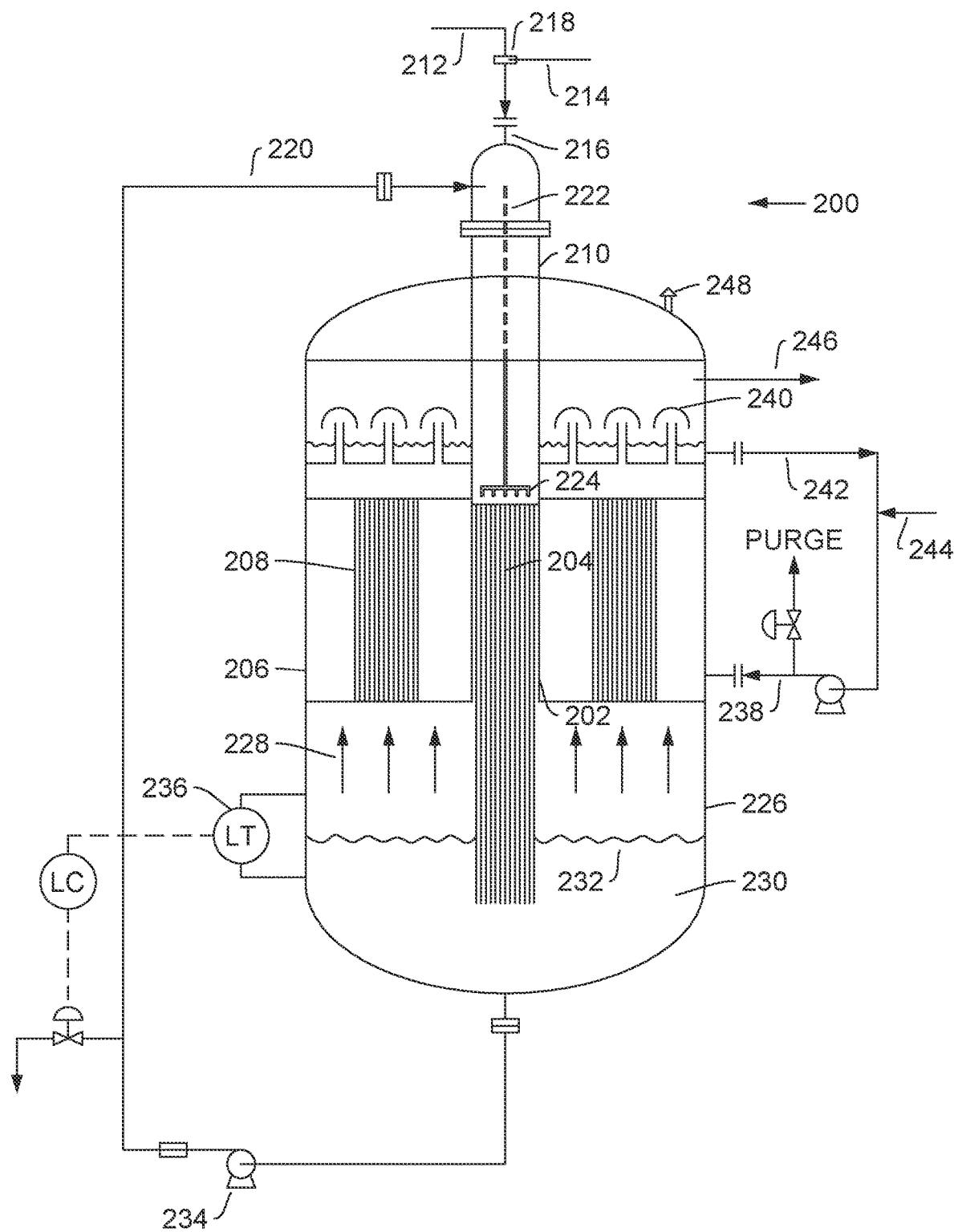
FIG. 2 illustrates a hydrocarbon desulfurization vessel containing catalytic carbon fibers.

FIG. 2 illustrates one embodiment of a hydrocarbon desulfurization vessel 200 containing catalytic carbon fibers described herein. As illustrated, hydrocarbon desulfurization vessel 200 contains a caustic treatment section 202 containing fiber bundle 204 and an oxidation section 206 containing catalytic carbon fibers 208. Conduit 210 may contain caustic treatment section 202 containing fiber bundle 204 which may physically separate caustic treatment section 202 from oxidation section 206 and provide a flow path for fluid to flow through. Oxidation section 206 containing catalytic carbon fibers 208 may be disposed in an annular space formed between conduit 210 and the walls of vessel 200.

The hydrocarbon feed 212 containing mercaptan sulfur compounds to be treated may be mixed with oxidizer 214 and introduced into conduit 210. In some examples, sparger 218 may be utilized to distribute oxidizer 214 into hydrocarbon feed 21. Oxidizer 214 may include any suitable oxidizer, including air, oxygen, hydrogen peroxide, or any other oxygen containing gas or compound which releases oxygen. Generally, the amount of oxidizer 214 introduced should be sufficient to oxidize all mercaptan sulfur compounds present in hydrocarbon feed 212. Once the hydrocarbon/oxidizer feed is introduced into conduit 210, it may flow through conduit 210 and contact fiber bundle 204. Caustic stream 220 may be introduced into conduit 210 such that the hydrocarbon/oxidizer feed may be mixed with caustic stream 220 before contacting fiber bundle 204. In some examples, it may be desired to disperse the caustic from caustic stream 220 to enhance contact between the hydrocarbon phase from hydrocarbon feed 212 and the aqueous phase from caustic stream 220. In such examples, line 222 may be connected to a distributor 224 disposed above fiber bundle 204 whereby caustic stream 220 is connected to distributor 224 via line 222, and the hydrocarbon/oxidizer feed may mix with the caustic from caustic stream 220 above fiber bundle 204.

In either example, hydrocarbon/oxidizer feed and caustic from caustic stream 220 may contact fiber bundle 204 which may cause the aqueous caustic to wet the individual fibers of fiber bundle 204. The aqueous caustic solution will form a film on fibers 204 which will be dragged downstream through conduit 210 by passage of hydrocarbon through same conduit. Both liquids may be discharged into separation zone 226 of the vessel 200. The volume of the hydrocarbon will be greater because the aqueous caustic passes through the fiber bundle at a lower volumetric flow rate than the hydrocarbon. During the relative movement of the hydrocarbon with respect to the aqueous caustic film on the fibers, a new interfacial boundary between the hydrocarbon and the aqueous caustic solution is continuously being formed, and as a result fresh aqueous caustic solution is brought in contact with this surface and allowed to react with the mercaptan sulfur or other impurities such as phenolics, naphthenic acid and other organic acids in the hydrocarbon. Mercaptan sulfur present in the hydrocarbon feed may be reacted with the caustic to produce mercaptides as shown in Reaction 1.

In separation zone 226, the aqueous caustic solution and hydrocarbon may collect in the lower portion of the vessel 200 and separate into hydrocarbon phase 228 and caustic phase 230. The interface 232 within vessel 200 may be kept at a level above the bottom of the downstream end of fiber bundle 204 so that the aqueous caustic film can be collected directly in the bottom of vessel 200 without it being dispersed into the hydrocarbon phase 228. Most of the phenolate or naphthenate impurities which may cause plugging in a packed bed are thus removed from the hydrocarbon in the caustic phase. Not only does this increase oxidation efficiency but reduces maintenance costs as well. However, some impurities may remain in the hydrocarbon which may be necessary to further treat the with caustic solution in oxidation section 206. Caustic phase 230 may be withdrawn from vessel 200 via pump 234 and may be returned to conduit 210 via caustic stream 220. The height of interface 232 within vessel 200 may be controlled by level controls system 236 which may include a level sensor, a level controller, and a purge valve, which may be configured to keep interface 232 at a level above the downstream end of fiber bundle 204.

From separation zone 226, hydrocarbon phase 228 may flow upwards into oxidation section 206, whereby the hydrocarbon phase 228 may contact catalytic carbon fibers 208. Additional caustic, if necessary, may be introduced into oxidation section 206 via line 238. A distribution grid may be present in oxidation section 206 which may distribute caustic from line 238 into oxidation section 206. In oxidation section 206 mercaptides, water, and oxygen may react according to Reaction 2 in the presence of the catalytic carbon fibers to produce disulfide oil, regenerated caustic, and water which may flow upwards through oxidation section 206. The additional caustic and hydrocarbon may be in contact and in concurrent flow through oxidation section 206. At the upper end of the catalytic carbon fibers, the additional caustic may be separated from the hydrocarbon by a liquid separator device such as chimney type trays in separation section 240. While chimney type trays are illustrated, there may be many alternative types of liquid separators can be used such as overflow weirs, for example. The additional hydroxide may be collected in separation section 240 and be drawn off as stream 242 to be re-introduced into oxidation section 206. Makeup caustic 244 may be added intermittently and a caustic purge may be utilized as needed. Hydrocarbon product 246 may be withdrawn from the top of separation section 240. Off-gas buildup in vessel 200 may be drawn off through line 248 and be processed in downstream units.

Figure 3:
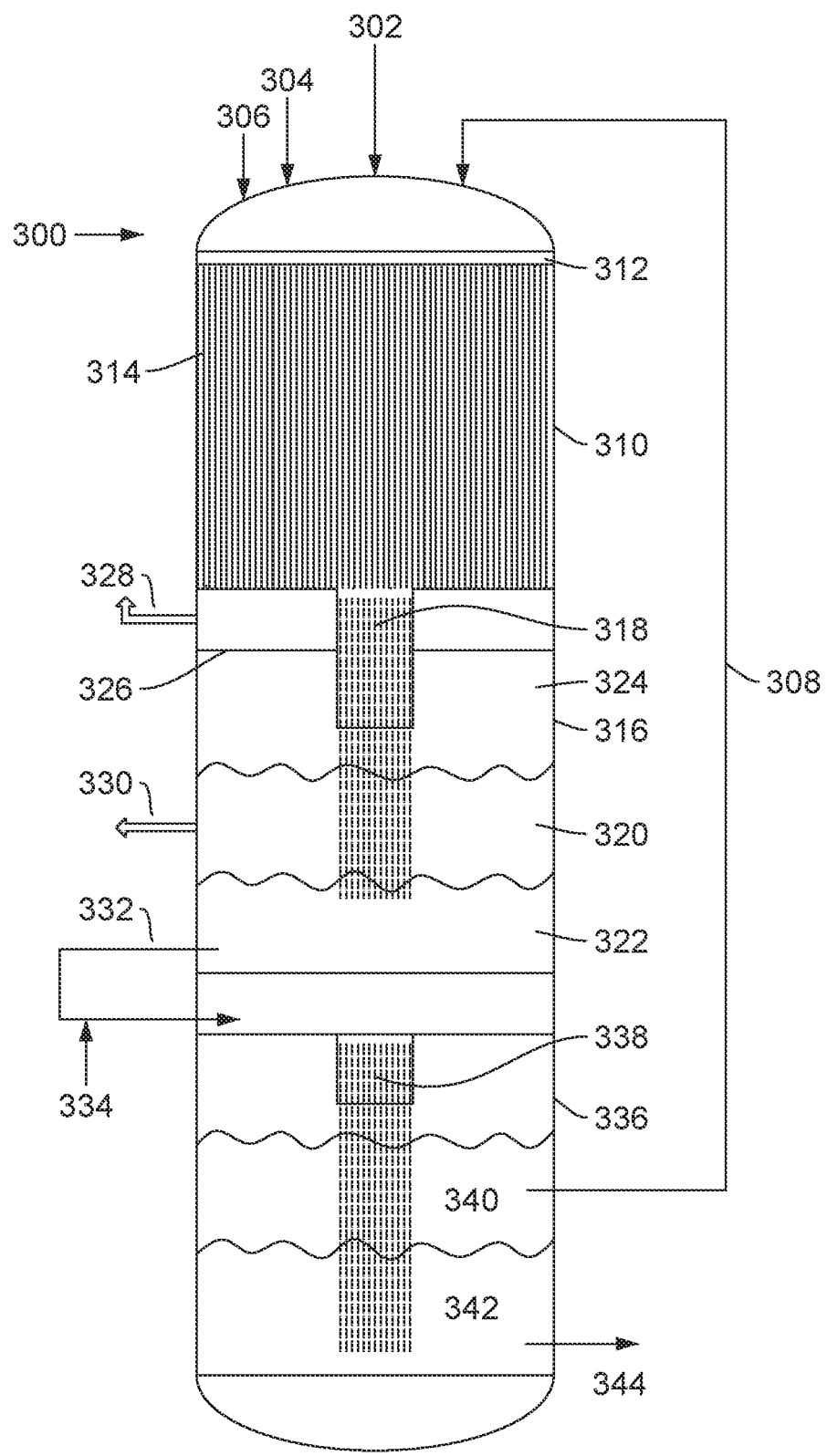
FIG. 3 illustrates a hydrocarbon desulfurization vessel containing catalytic carbon fibers.

FIG. 3 illustrates another embodiment of a caustic regeneration vessel 300 containing catalytic carbon fibers described herein. FIG. 3 illustrates a process conducted in a single vessel where a caustic feed 302, oxidizer 304, hydrocarbon stream 306, and, optionally, solvent stream 308 are introduced into oxidation section 310. Hydrocarbon stream 306 may include any hydrocarbons such as a fuel gas, for example. Oxidizer 304 may include any suitable oxidizer, including air, oxygen, hydrogen peroxide, or any other oxygen containing gas or compound which releases oxygen. Each of the streams may be introduced into vessel 300 through distributor 312 which may distribute the feeds into oxidation section 310. Oxidation section 310 contains catalytic carbon fibers 314 arranged to receive the feeds from distributor 312.

In oxidation section 310, the caustic from caustic feed 302 and solvent from solvent stream 308 may contact catalytic carbon fibers 314 which may cause the aqueous caustic to wet the individual fibers of catalytic carbon fibers 314. The aqueous caustic solution will form a film on catalytic carbon fibers 314 which will be dragged downstream through oxidation zone 310 by passage of oxidizer 304 through vessel 300. During the relative movement of oxidizer 304 with respect to the aqueous caustic film on the fibers, a new interfacial boundary between the oxidizer and the aqueous caustic solution is continuously being formed, and as a result fresh aqueous caustic solution is brought in contact with this surface and allowed to react with the mercaptide sulfur or other impurities such as phenolics, naphthenic acid and other organic acids in the hydrocarbon. The mercaptides react with oxygen provided by oxidizer 304 as shown in Reaction 2 in the presence of catalytic carbon fibers 314 to produce disulfide oil, regenerated caustic, and water.

The oxidation of mercaptides into disulfide oil occurring within the oxidation section 310 may results in a mixture composed of continuous phase caustic, discontinuous phase organic (disulfide oil, and solvent if present) droplets dispersed in the caustic phase, and gas (nitrogen and unreacted oxygen from air). The mixture of products, unreacted reactants, and inert species may exit oxidation section 310 and contact fiber bundle 318 and flow into separation section 316. In some instances, fiber bundle 318 may be composed of the fiber bundle 314 but longer so as to construe one single bundle rather than two separate bundles. The fiber bundle may promote phase separation as explained previously. In separation section 316, the aqueous caustic and hydrocarbon may collect in the lower portion of separation section 316 and separate into hydrocarbon phase 320, caustic phase 322, and gas phase 324. Gas from oxidizer 304 disengages from liquid stream at the outlet of fiber bundle 318 and exits through a mist eliminator 326 as off-gas 328. The two immiscible liquids, as a single stream of aqueous and hydrocarbon, flow downwards along fiber bundle 318 during which organic hydrocarbon droplets coalesce and form hydrocarbon phase 320 containing the majority of generated disulfide oil, while the aqueous caustic adheres to the fibers and flows further downward to form caustic phase 322.

Hydrocarbon phase 320 containing the hydrocarbons from solvent feed 308, if present, as well as the generated disulfide oil may be withdrawn as stream 330. Caustic phase 322 may contain a residual amount of disulfide oil which may be further removed before the caustic is reused. Caustic phase 322 may be withdrawn as stream 332 which may be mixed with fresh solvent stream 334 before contacting fiber bundle 338 and flowing into separation section 336. In separation section 336, the aqueous caustic from caustic phase 322 and solvent from solvent stream 334 may collect in the lower portion of separation section 336 and separate into solvent phase 340 and caustic phase 342. Solvent phase 340 may contain the bulk of any residual disulfide oil present in caustic phase 322 after flowing through fiber bundle 338. Solvent phase 340 may be withdrawn and recycled to vessel 300 as solvent stream 308. Regenerated caustic phase 342 may be withdrawn and recycled as stream 344 and reused.

Figure 4:
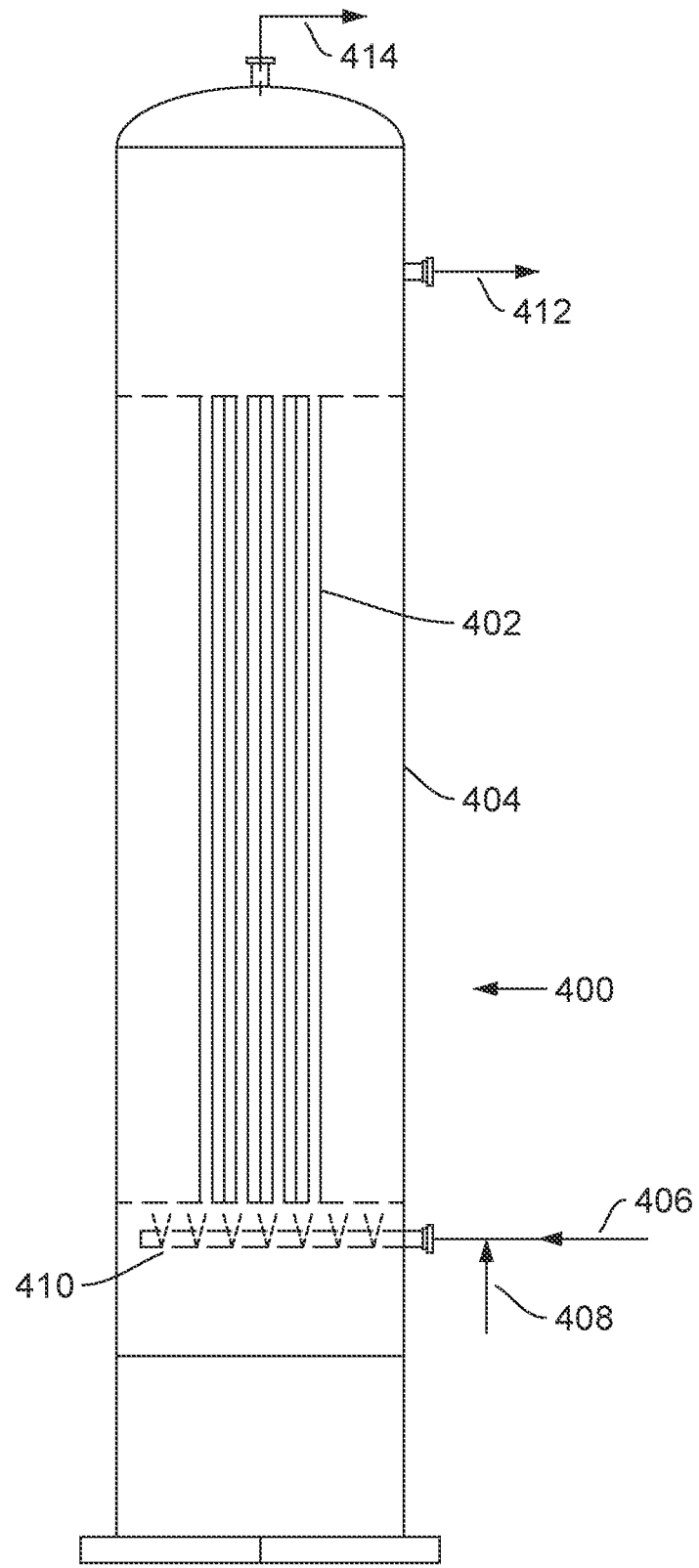
FIG. 4 illustrates a standalone caustic regeneration unit containing catalytic carbon fibers.

FIG. 4 illustrates a standalone caustic regeneration unit 400 comprising catalytic carbon fibers 402 disposed in oxidation zone 404. Rich caustic stream 406, containing mercaptides and/or sulfides, enters the bottom of the vessel. Oxidizer 408 is introduced into caustic regeneration unit 400 through distributor 410 and mixes with the rich caustic. Rich caustic stream may be from any unit, including those previously described herein, which contains a rich caustic and mercaptides. Oxidizer 408 may include any suitable oxidizer, including air, oxygen, hydrogen peroxide, or any other oxygen containing gas or compound which releases oxygen. The mixture of oxidizer 408 and rich caustic stream 406 may contact catalytic carbon fibers 402 which may cause the aqueous caustic to wet the individual fibers of catalytic carbon fibers 402. Mercaptides present in caustic stream 406 further react with oxygen provided by oxidizer 408 as shown in Reaction 2 in the presence of catalytic carbon fibers 402 to produce disulfide oil, regenerated caustic, and water which may flow upwards along catalytic carbon fibers 402. The resultant disulfide oil, regenerated caustic, or both may be withdrawn from regeneration unit 400 as stream 412. Although illustrated in FIG. 4 as one stream, stream 412 may be two or more streams such as in previous figures where an aqueous phase and oleaginous phase are separately withdrawn. Off-gas 414 may also be withdrawn from caustic regeneration unit 400.

FIG. 5a illustrates a standalone caustic regeneration unit 500 comprising catalytic fibers 502 disposed in an oxidation zone 504. Rich caustic stream 506, containing mercaptides and/or sulfides enters the top of the vessel. Oxidizer 508 enters above the distributor tray 510. Oxidizer 508 may include any suitable oxidizer, including air, oxygen, hydrogen peroxide, or any other oxygen containing gas or compound which releases oxygen. An example of the distributor tray is shown in FIG. 5b but other variations may apply equally well. On the distributor tray 510, a solvent stream 520 may also be introduced above the distributor tray 510. Distributor tray 510 distributes these phases onto the catalytic fiber 502. In some embodiments, riser pipes 516 may be disposed on distributor tray 510. The mixture of at least oxidizer 508 and rich caustic stream 506 may contact the catalytic carbon fiber 502 which may cause the aqueous caustic to wet the individual fibers of catalytic carbon fibers 502. Mercaptides present in caustic stream 506 further react with oxygen provided by oxidizer 508 as shown in Reaction 2 in the presence of catalytic carbon fibers 502 to produce disulfide oil, regenerated caustic, and water which may flow downwards along catalytic carbon fibers 502. The resultant disulfide oil, regenerated caustic, or both may be withdrawn from regeneration unit 500 as stream 512. Although illustrated in FIG. 5 as one stream, stream 512 may be two or more streams such as in previous figures where an aqueous phase and oleaginous phase are separately withdrawn. Off-gas 514 may also be withdrawn from caustic regeneration unit 500. FIG. 5b shows a top view of distributor tray 510 with riser pipes 516 and holes 518 to allow for the fluids to flow through the distributor tray 510.

Accordingly, the present disclosure may provide methods, systems, and apparatus that may relate to fluid-fluid contacting. The methods, systems. and apparatus may include any of the various features disclosed herein, including one or more of the following statements.

Statement 1. A method of producing a catalytic carbon fiber comprising: providing a carbon fiber and an aminated macrocycle, mixing the carbon fiber and the aminated macrocycle with a solvent; and reacting the carbon fiber and the aminated macrocycle to form an amide bond between the carbon fiber and the aminated macrocycle thereby forming the catalytic carbon fiber.

Statement 2. The method of statement 1, wherein the aminated macrocycle comprises an organometallic macrocycle and an amine group grafted to the organometallic macrocycle.

Statement 3. The method of statement 2, wherein the organometallic macrocycle comprises an unsubstituted metal phthalocyanine a substituted metal phthalocyanine, or combinations thereof.

Statement 4. The method of statement 3 wherein the substituted metal phthalocyanine is substituted with at least one of a halogen group, a hydroxyl group, an alkyl group, an aryl group, a thiol group, an alkoxy group, a nitrosyl group, sulfonic group, or combinations thereof.

Statement 5. The method of statements 3-4, wherein the unsubstituted metal phthalocyanine or the substituted metal phthalocyanine comprises a metal selected from vanadium (V), manganese (Mn), iron (Fe), cobalt (Co), nickel (Ni), copper (Cu), zinc (Zn), ruthenium (Ru), rhodium (Rh), palladium (Pd), silver (Ag), and combinations thereof.

Statement 6. The method of claim 2, wherein the amine group comprises an amine with a carbon length from C2-C20.

Statement 7. The method of any of statements 1-6, wherein the solvent comprise at least one solvent selected from the group consisting of water, pyridine, DMSO, DMF, THF, ethanol, acetonitrile, chloroform, ethylene glycol, methanol, benzene, and combinations thereof.

Statement 8. The method of statement 2, wherein the amine group comprises a reaction product of at least one amine compound selected from ethylenediamine, propane-1,3-diamine, butane-1,4-diamine, pentane-1,5-diamine, hexamethylenediamine, diethylenetriamine, benzene-1,3,5-triamine, and combinations thereof.

Statement 9. The method of any of statements 1-8 1, wherein the aminated macrocycle comprises at least one of mono-amino cobalt phthalocyanine, di-amino cobalt phthalocyanine, tri-amino cobalt phthalocyanine, tetra-amino cobalt phthalocyanine, and combinations thereof.

Statement 10. The method of any of statements 1-9, wherein the reacting is carried out at a temperature in a range of about 100° C. to about 200° C.

Statement 11. A method of producing a catalytic carbon fiber comprising: providing a carbon fiber; reacting the carbon fiber with a chlorinating agent to produce a carbon fiber comprising acyl chloride; and reacting the carbon fiber comprising acyl chloride with an aminated macrocycle to form an amide bond between the carbon fiber comprising acyl chloride and the aminated macrocycle thereby forming the catalytic carbon fiber.

Statement 12. The method of statement 11, wherein the chlorinating agent comprises a chlorinating agent selected from the group consisting of thionyl chloride, phosphorous trichloride, terephthaloyl chloride and combinations thereof.

Statement 13. The method of any statements 11-12, wherein the aminated macrocycle comprises an organometallic macrocycle and an amine group grafted to the organometallic macrocycle.

Statement 14. The method of statement 13, wherein the organometallic macrocycle comprises an unsubstituted metal phthalocyanine a substituted metal phthalocyanine, or combinations thereof.

Statement 15. The method of statements 13-14 wherein the substituted metal phthalocyanine is substituted with at least one of a halogen group, a hydroxyl group, an alkyl group, an aryl group, a thiol group, an alkoxy group, a nitrosyl group, sulfonic group, or combinations thereof.

Statement 16. The method of statements 13-15, wherein the unsubstituted metal phthalocyanine or the substituted metal phthalocyanine comprises a metal selected from vanadium (V), manganese (Mn), iron (Fe), cobalt (Co), nickel (Ni), copper (Cu), zinc (Zn), ruthenium (Ru), rhodium (Rh), palladium (Pd), silver (Ag), and combinations thereof.

Statement 17. The method of any of statements 11-16, further comprising removing the chlorinating agent from the carbon fiber comprising acyl chloride and dispersing the carbon fiber comprising acyl chloride in a solvent prior to the step of reacting the carbon fiber comprising acyl chloride with an aminated macrocycle.

Statement 18. The methods of any of statements 11-17, wherein the step of reacting the carbon fiber comprising acyl chloride with an aminated macrocycle comprises reacting in the presence of pyridine.

Statement 19. A method of producing a catalytic carbon fiber comprising: providing a carbon fiber; reacting the carbon fiber with a coupling agent to produce a functionalized carbon fiber; and reacting the functionalized carbon fiber with an aminated macrocycle to form an amide bond between the carbon fiber and the aminated macrocycle thereby forming the catalytic carbon fiber.

Statement 20 The method of statement 19, wherein the coupling agent comprises carbodiimide, benzotriazole, or combinations thereof.

Statement 21. A method of producing a catalytic carbon fiber comprising: providing a carbon fiber; providing an enzyme capable of catalyzing an amide bond formation; and reacting the carbon fiber with an aminated macrocycle in the presence of the enzyme to form a bond between the carbon fiber and the aminated macrocycle thereby forming the catalytic carbon fiber.

Statement 22. The method of statement 21 wherein the enzyme comprises an enzyme selected from the group consisting of proteases, subtilisin, acylases, amidases lipases, and combinations thereof.

EXAMPLES

To facilitate a better understanding of the present disclosure, the following illustrative examples of some of the embodiments are given. In no way should such examples be read to limit, or to define, the scope of the disclosure.

Example 1

In this Example, catalytic carbon fiber was prepared and evaluated. The catalytic carbon fiber was prepared by measuring 0.5 g of tetra-amino cobalt phthalocyanine (TACoPc) and dissolving in 125 mL of dimethyl sulfoxide (DMSO). 4 grams of virgin carbon fiber were added to the DMSO solution and heated at 135° C. for 5 hours. Thereafter, the carbon fiber was washed with DMSO followed by DI water and dried at 60° C.

Kerosene containing 330 ppm of mercaptan sulfur was prepared. A 3 gram sample of the tetra-amino cobalt phthalocyanine modified carbon fiber from this example and 150 mL of the mercaptan containing kerosene was mixed vigorously in a shaker bath at 300 rpm and 38° C. Kerosene samples were withdrawn over the course of 30 minutes and the mercaptan concentration in each sample was determined by titration. The second order mercaptan oxidation rate constant was calculated to be $2.9*10^{-4}$ (1/M*min).

Example 2

In this Example, catalytic carbon fiber was prepared and evaluated. The catalytic carbon fiber was prepared by measuring 0.5 g of mono-amino cobalt phthalocyanine (MA-CoPc) and dissolving in 125 mL of dimethyl sulfoxide (DMSO). 4 grams of virgin carbon fiber were added to the DMSO solution and heated at 135° C. for 5 hours. Thereafter, the carbon fiber was washed with DMSO followed by DI water and dried at 60° C.

Kerosene containing 330 ppm of mercaptan sulfur was prepared. A 3 gram sample of the mono-amino cobalt phthalocyanine modified carbon fiber from this example and 150 mL of the mercaptan containing kerosene was mixed vigorously in a shaker bath at 300 rpm and 38° C. Kerosene samples were withdrawn over the course of 30 minutes and the mercaptan concentration in each sample was determined by titration. The second order mercaptan oxidation rate constant was calculated to be $6.3*10^{-4}$ (1/M*min).

Example 3

In this Example, catalytic carbon fiber was prepared and evaluated. The catalytic carbon fiber was prepared by measuring 0.5 g of mono-amino cobalt phthalocyanine (MA-CoPc) and dissolving in 125 mL of dimethylformamide (DMF). 4 grams of virgin carbon fiber were added to the DMF solution and heated at 135° C. for 5 hours. Thereafter, the carbon fiber was washed with DMF followed by DI water and dried at 60° C.

Kerosene containing 330 ppm of mercaptan sulfur was prepared. A 3 gram sample of the mono-amino cobalt phthalocyanine modified carbon fiber from this example and 150 mL of the mercaptan containing kerosene was mixed vigorously in a shaker bath at 300 rpm and 38° C. Kerosene samples were withdrawn over the course of 30 minutes and the mercaptan concentration in each sample was determined by titration. The second order mercaptan oxidation rate constant was calculated to be $7.1*10^{-4}$ (1/M*min).

Example 4

In this Example, catalytic carbon fiber was prepared and evaluated. The catalytic carbon fiber was prepared by measuring 0.5 g of mono-amino cobalt phthalocyanine (MA-CoPc) and dissolving in 125 mL of DMSO. 4 grams of virgin carbon fiber were added to the DMSO solution and heated at 160° C. for 5 hours. Thereafter, the carbon fiber was washed with DMSO followed by DI water and dried at 60° C.

Kerosene containing 330 ppm of mercaptan sulfur was prepared. A 3 gram sample of the mono-amino cobalt phthalocyanine modified carbon fiber from this example and 150 mL of the mercaptan containing kerosene was mixed vigorously in a shaker bath at 300 rpm and 38° C. Kerosene samples were withdrawn over the course of 30 minutes and the mercaptan concentration in each sample was determined by titration. The second order mercaptan oxidation rate constant was calculated to be $10.5*10^{-4}$ (1/M*min).

Example 5

In this Example, catalytic carbon fiber was prepared and evaluated. The catalytic carbon fiber was prepared by mixing 4 grams of virgin carbon fiber with 125 mL thionyl chloride and refluxed at 65° C. for 24 hours. Thereafter, the thionyl chloride was removed by distillation. A solution was prepared containing 0.25 g of TACoPc and 125 mL DMF. The thionyl chloride treated carbon fiber and 1 mL pyridine were added to the DMF solution and heated at 80° C. for 20 hours. The carbon fiber was washed with DMSO and DI water and dried at 60° C.

Kerosene containing 330 ppm of mercaptan sulfur was prepared. A 3 gram sample of the mono-amino cobalt phthalocyanine modified carbon fiber from this example and 150 mL of the mercaptan containing kerosene was mixed vigorously in a shaker bath at 300 rpm and 38° C. Kerosene samples were withdrawn over the course of 30 minutes and the mercaptan concentration in each sample was determined by titration. The second order mercaptan oxidation rate constant was calculated to be $3.4*10^{-4}$ (1/M*min).

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method of producing a catalytic carbon fiber comprising:
   providing a carbon fiber and an aminated macrocycle,
   mixing the carbon fiber and the aminated macrocycle with a solvent; and
   reacting the carbon fiber and the aminated macrocycle to form an amide bond between the carbon fiber and the aminated macrocycle thereby forming the catalytic carbon fiber.

2. The method of claim 1, wherein the aminated macrocycle comprises an organometallic macrocycle and an amine group grafted to the organometallic macrocycle.

3. The method of claim 2, wherein the organometallic macrocycle comprises an unsubstituted metal phthalocyanine, a substituted metal phthalocyanine, or combinations thereof.

4. The method of claim 3 wherein the substituted metal phthalocyanine is substituted with at least one of a halogen group, a hydroxyl group, an alkyl group, an aryl group, a thiol group, an alkoxy group, a nitrosyl group, sulfonic group, or combinations thereof.

5. The method of claim 3, wherein the unsubstituted metal phthalocyanine or the substituted metal phthalocyanine comprises a metal selected from vanadium (V), manganese (Mn), iron (Fe), cobalt (Co), nickel (Ni), copper (Cu), zinc (Zn), ruthenium (Ru), rhodium (Rh), palladium (Pd), silver (Ag), and combinations thereof.

6. The method of claim 2, wherein the amine group comprises an amine with a carbon length from C2-C20.

7. The method of claim 1, wherein the solvent comprises at least one solvent selected from the group consisting of water, pyridine, DMSO, DMF, THF, ethanol, acetonitrile, chloroform, ethylene glycol, methanol, benzene, and combinations thereof.

8. The method of claim 2, wherein the amine group comprises a reaction product of at least one amine compound selected from ethylenediamine, propane-1,3-diamine, butane-1,4-diamine, pentane-1,5-diamine, hexamethylenediamine, diethylenetriamine, benzene-1,3,5-triamine, and combinations thereof.

9. The method of claim 1, wherein the aminated macrocycle comprises at least one of mono-amino cobalt phthalocyanine, di-amino cobalt phthalocyanine, tri-amino cobalt phthalocyanine, tetra-amino cobalt phthalocyanine, and combinations thereof.

10. The method of claim 1, wherein the reacting is carried out at a temperature in a range of about 100° C. to about 200° C.

11. A method of producing a catalytic carbon fiber comprising:
    providing a carbon fiber;

reacting the carbon fiber with a chlorinating agent to produce a carbon fiber comprising acyl chloride; and reacting the carbon fiber comprising acyl chloride with an aminated macrocycle to form an amide bond between the carbon fiber comprising acyl chloride and the aminated macrocycle thereby forming the catalytic carbon fiber.

12. The method of claim 11, wherein the chlorinating agent comprises a chlorinating agent selected from the group consisting of thionyl chloride, phosphorous trichloride, terephthaloyl chloride and combinations thereof.

13. The method of claim 11, wherein the aminated macrocycle comprises an organometallic macrocycle and an amine group grafted to the organometallic macrocycle.

14. The method of claim 13, wherein the organometallic macrocycle comprises an unsubstituted metal phthalocyanine a substituted metal phthalocyanine, or combinations thereof.

15. The method of claim 14 wherein the substituted metal phthalocyanine is substituted with at least one of a halogen group, a hydroxyl group, an alkyl group, an aryl group, a thiol group, an alkoxy group, a nitrosyl group, sulfonic group, or combinations thereof.

16. The method of claim 14, wherein the unsubstituted metal phthalocyanine or the substituted metal phthalocyanine comprises a metal selected from vanadium (V), manganese (Mn), iron (Fe), cobalt (Co), nickel (Ni), copper (Cu), zinc (Zn), ruthenium (Ru), rhodium (Rh), palladium (Pd), silver (Ag), and combinations thereof.

17. The method of claim 11, further comprising removing the chlorinating agent from the carbon fiber comprising acyl chloride and dispersing the carbon fiber comprising acyl chloride in a solvent prior to the step of reacting the carbon fiber comprising acyl chloride with an aminated macrocycle.

18. The method of claim 11, wherein the step of reacting the carbon fiber comprising acyl chloride with an aminated macrocycle comprises reacting in the presence of pyridine.

19. A method of producing a catalytic carbon fiber comprising:

providing a carbon fiber;

reacting the carbon fiber with a coupling agent to produce a functionalized carbon fiber; and reacting the functionalized carbon fiber with an aminated macrocycle to form an amide bond between the carbon fiber and the aminated macrocycle thereby forming the catalytic carbon fiber.

20. The method of claim 19, wherein the coupling agent comprises carbodiimide, benzotriazole, or combinations thereof.

21. A method of producing a catalytic carbon fiber comprising:

providing a carbon fiber;

providing an enzyme capable of catalyzing an amide bond formation; and reacting the carbon fiber with an aminated macrocycle in the presence of the enzyme to form a bond between the carbon fiber and the aminated macrocycle thereby forming the catalytic carbon fiber.

22. The method of claim 21 wherein the enzyme comprises an enzyme selected from the group consisting of proteases, subtilisin, acylases, amidases, lipases, and combinations thereof.

* * * * *